United States Patent [19]

Krupa

[11] 3,980,070

[45] Sept. 14, 1976

[54] HEATING PACK CONTAINING A GRANULAR CHEMICAL COMPOSITION

[75] Inventor: Calvin S. Krupa, Osseo, Minn.

[73] Assignee: Scotty Manufacturing Company, Osseo, Minn.

[22] Filed: Jan. 8, 1975

[21] Appl. No.: 539,272

[52] U.S. Cl. ................................. 126/263; 44/3 A; 128/403; 206/219; 229/62.5; 150/7; 252/74
[51] Int. Cl.² .............................................. F24J 1/02
[58] Field of Search .............. 126/263; 44/3 R, 3 A, 44/3 B, 3 C; 62/4, 530; 128/403; 206/219; 229/62.5; 150/2.1, 7, 9; 252/74

[56] References Cited
UNITED STATES PATENTS

| 683,896 | 10/1901 | Bates | 126/263 |
|---|---|---|---|
| 1,434,576 | 11/1922 | Wertheimer | 126/263 |
| 1,525,168 | 2/1925 | Davidson | 44/3 A |
| 1,613,120 | 1/1927 | Oneal | 44/3 R |
| 1,652,457 | 12/1927 | Reach | 150/7 |
| 1,659,185 | 2/1928 | Baker | 126/263 |
| 1,819,807 | 8/1931 | Baysinger | 126/263 |
| 2,040,406 | 5/1936 | Reed | 44/3 A |
| 2,132,681 | 10/1938 | Davis et al. | 44/3 A |
| 2,157,169 | 5/1939 | Foster | 126/263 |
| 2,800,269 | 7/1957 | Smith | 62/530 |

Primary Examiner—William F. O'Dea
Assistant Examiner—Ronald C. Capossela
Attorney, Agent, or Firm—Merchant, Gould, Smith, Edell, Welter & Schmidt

[57] ABSTRACT

A heating pack for use with an improved granular chemical composition which produces heat when water is added. The heating pack utilizes an inner and outer bag, the inner bag containing the granular composition and having a closure flap which is partially sealed by means of a barrier envelope which allows water to be added to the inner bag while preventing spillage of the granular composition. The chemical composition contains an improved oxidizing mixture in combination with iron particles which yields a relatively high heat output to weight ratio for the heating pack.

4 Claims, 6 Drawing Figures

HEATING PACK CONTAINING A GRANULAR CHEMICAL COMPOSITION

BACKGROUND OF THE INVENTION

1. Field of the Invention

A heat producing pack utilizing an outer bag and a removable inner bag which contains a chemical composition to produce an exothermic reaction when moistened.

2. Description of the Prior Art

It has long been known that the combination of certain chemical elements produces an exothermic reaction. Many such combinations include ferrous materials such as iron filings and other chemicals which release heat when they are combined with an aqueous solution. Such chemical compositions are frequently utilized in combination with a bag-like container to form a heating pack which can be selectively activated by adding water to the chemical composition and deactivated by allowing the chemical composition to dry.

Presently available chemical-composition heating packs are frequently limited in their usefulness either by the limited amount of heat per unit weight which the chemical composition yields when reacting with water, by the useful life of the chemical composition, or by the structure of the bag which contains the chemical composition. In particular, when a ferrous material is utilized as part of the chemical composition, the overall weight of the heating pack is increased significantly. In the past, the limitations on efficiency of the oxidizing mixture utilized with the ferrous material have required a relatively large amount of the ferrous material and thus the weight of the heating pack has frequently been a limiting factor in the design of such devices. Because of the limitations in the efficiency of the oxidizing mixture, the heat output of the heating pack frequently could be increased only by significantly increasing the amount of ferrous material which is utilized. In addition to adding weight to the heating pack, the volume of the heating pack is increased significantly with the need for larger amounts of the ferrous material. Presently available designs for heating packs often require a relatively long time to heat up and sometimes produce an undesirable odor.

Several methods of containing a granular chemical composition are presently used for heating packs. Typically, the heating pack container will be a bag-like enclosure having a flap which covers the opening and through which water is added to the granular chemical composition. To suitably contain the granular composition while preventing its spillage, various devices have been utilized, including sealed capsules containing the activating liquid which are punctured for use. In addition, relatively complex funneling apparatus has been used in combination with bags. The sealed capsule type containers generally are not reusable and the complex funnel apparatus results in increased manufacturing costs. Where a simple flap or snapflap design is utilized as the only means for enclosing the chemical composition, the granular material may spill out of the bag. This is particularly so where it is advantageous to shake or agitate the mixture to properly mix the dry chemicals with the liquid.

SUMMARY

The present invention is an improved heating pack containing a granular chemical composition. The granular composition includes a suitable ferrous metal and an oxidizing agent which is described subsequently. When water is added to this chemical composition, an exothermic reaction results which produces heat useful as a hand warmer and the like. The particular combination of chemical elements provides an improved chemical mix which results in faster heating of the composition, a lower level of objectionable odor and reduced weight through a reduction in the amount of iron filings which are necessary.

The chemical composition is contained in an inner bag which is encloseable in a second outer bag. The inner bag comprises a rectangular bottom portion and a tapered flap portion which has a liquid fill opening. A barrier-producing envelope sewn in the flap portion of the inner bag prevents spillage of the granular material while allowing water to be added through openings in the envelope. The openings are effectively closed to the passage of granular material by means of a closure rivet and folding of the flap portion. This twobag container in combination with the improved chemical composition provides a heating pack which is economical to produce and use and which produces a relatively fast heating cycle. When the chemical composition is allowed to dry, the exothermic reaction is stopped and the heating pack can be recycled repeatedly by adding water to the chemical composition for each use.

The preferred chemical composition comprises an oxidizing component and a ferrous metal component. The ferrous metal component preferably consists essentially of cast iron filings. About 5 to about 10 parts by weight of the oxidizing component are combined (e.g. dry mixed) with each 100 parts by weight of the ferrous component. The oxidizing component preferably comprises:

20–50% by weight of cupric carbonate,
20–60% by weight of a suitable water soluble metal halide salt (e.g. NaCl),
15–40% by weight of citric acid, and
6–12% by weight of an alkali metal chlorate (e.g. $KClO_3$).

DETAILED DESCRIPTION OF THE PREFERRED EMBODIMENT

Figure 1:
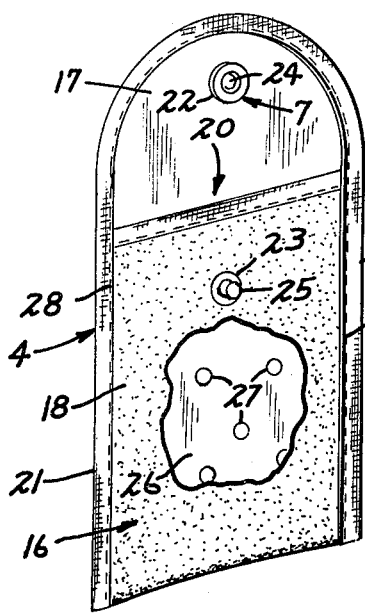
FIG. 1 is a perspective view of the heating pack outer bag.
Figure 2:
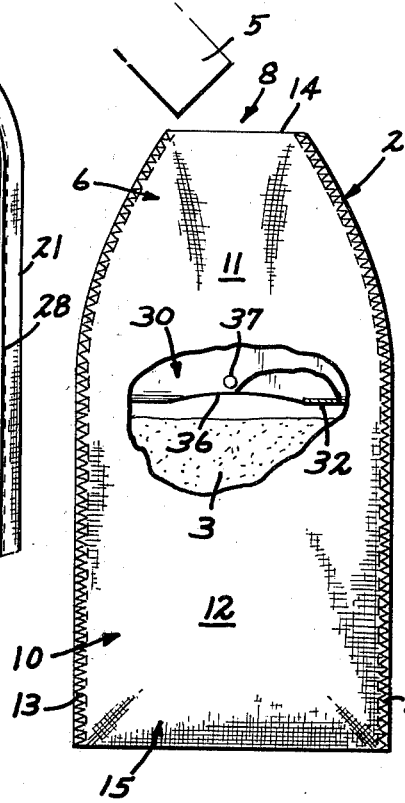
FIG. 2 is a front elevational view of the heating pack inner bag with portions cut away.
Figure 3:
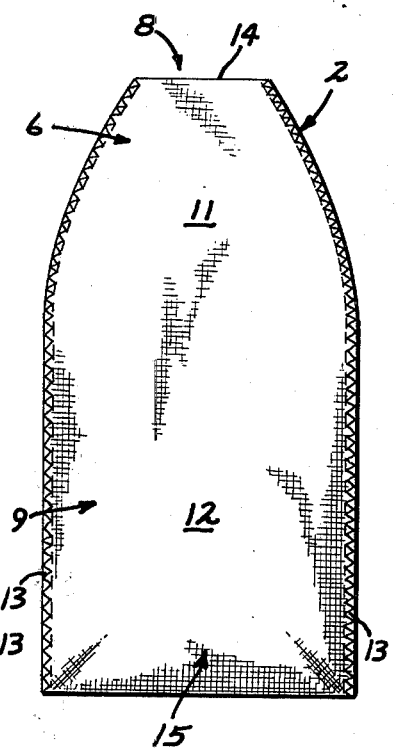
FIG. 3 is a back elevational view of the heating pack inner bag shown in FIG. 2.

It is the function of the present invention to provide a heating pack 1 which can be conveniently utilized to apply a constant source of flameless heat in a selected location. In the preferred embodiment shown in FIGS. 1–6, wherein like numerals refer to like structural elements, a granular chemical composition 3 is contained within an inner bag 2 and produces a relatively constant heat when the composition is activated by the addition of water. Inner bag 2 is designed to allow advantageous mixing of the water with the granular composition without spillage of the chemical composition from the bag. After the chemical composition 3 has been activated by the addition of water, the inner bag 2 is placed inside of an outer bag 4. Outer bag 4 has a closeable flap and is fabricated from a combination of materials which allow the heat generated within the bag to be conveniently and effectively transmitted to the exterior of outer bag 4.

In the preferred embodiment of the present invention, the heat producing chemical composition 3 is in a granular sand-like form and includes a relatively large amount of ferrous material in the form of iron filings. Chemical composition 3 will be described in detail later. When dry, chemical composition 3 is inert and produces no heat. When water is added to chemical composition 3 (e.g. from a water source 5) an exothermic chemical reaction is started which produces a generally constant level of heat. This process continues until the water contained within inner bag 2 is depleted by evaporation or chemical reaction. Heating pack 1 may be recycled by subsequent additions of water to produce additional periods of heating.

Referring to FIGS. 1-6, inner bag 2 is comprised of a flexible front panel 10 and a matching flexible back panel 9. Each of panels 9 and 10 has a generally rectangular bottom portion 12 and a tapered flap portion 11. Each of tapered flap portions 11 has a broad base with sides which curve inwardly to a narrow top edge 14. The two panels are joined together by stitching 13 which surrounds the periphery of the panels joining them together to form an enclosed bag-like container having a top portion 6 and a generally rectangular bottom portion 15 for retaining chemical composition 3. When front and pack panels 9 and 10 are sewn together, the top edges 14 of each of the panels is left unsewn so that a liquid fill opening 8 is formed along edge 14 between panels 9 and 10 to provide means for adding water to chemical composition 3 contained within inner bag 2.

In order for chemical composition 3 to chemically react with the water which is added to it and to dry for a cyclical exothermic reaction, it is desirable that the chemical composition be exposed to an adequate supply of air. In the preferred embodiment shown in FIGS. 2-6, front panel 10 and back panel 9 are each constructed of a porous cloth fabric which allows air to freely pass through the front and back panels to combine with the chemical composition 3. In addition, the construction of inner bag 2 allows some air to enter the bag through the liquid fill opening 8. Various other materials having adequate porosity (not shown) may be utilized for panels 9 and 10 to allow an adequate flow of air through the panels to chemical composition 3.

In the embodiment shown in FIGS. 2-6, inner bag 2 is designed to allow water to be freely added (e.g. from a water source 5) to the chemical composition 3 while at the same time preventing the spillage of the granular chemical composition 3 out of inner bag 2. Inner bag 2 is designed with bottom portion 15 and top portion 6 to accomplish this objective. Because back panel 9 and front panel 10 are fabricated from flexible materials, top portion 6 can be folded over the rectangular bottom portion 15 generally along a line which separates bottom portion 15 from top portion 6. This folding partially seals off bottom portion 15 which contains chemical composition 3. In effect, by folding over top portion 6, opposed front and back panels 9 and 10 are forced into generally abutting engagement with one another to close off bottom portion 15 and prevent spillage of the granular composition 3. This folding and sealing effect is shown diagrammatically in FIG. 5.

Because the front and back panels (9 and 10) of inner bag 2 are flexible, even when top portion 6 is folded down over rectangular bottom portion 15, the flexibility of the panels may allow the panels to wrinkle or otherwise spread apart providing an open passageway between bottom portion 15 and liquid fill opening 8 located in top portion 6. This would result in spillage of chemical composition 3. To prevent such spillage, a barrier envelope 30 is utilized. As is shown in detail in FIG. 6, barrier envelope 30 consists of two opposed side panels, each designated by the numeral 31, which are joined together at a bottom edge 32. In the preferred embodiment, bottom edge 32 is formed by folding a single piece of material which makes up both of side panels 31. It is the purpose of barrier envelope 30 to be positioned between the side panels of inner bag 2 adjacent the top portions 11. For this reason, the side panels 31 of barrier envelope 30 have essentially the same planform as the top portion 6 of inner bag 2. In assembling inner bag 2, barrier envelope 30 would be positioned between side panels 9 and 10 before the flap portions 11 of those panels were sewn together. When the flap portions 11 of panels 9 and 10 are sewn together, the stitching 13 would act to hold barrier envelope 30 in place within the top portion 6 of inner bag 2.

Each of side panels 31 of barrier envelope 30 has a generally flat top edge 33. As in the case of adjoining side panels 9 and 10, the top edges 33 of said panels 31 are not sewn together. In this manner, the liquid fill opening 8 in inner bag 2 is left open when barrier envelope 30 is sewn in place. The remainder of envelope 30 is essentially enclosed by stitching 13 along side edges 34 and closed bottom edge 32. A second opening is provided in barrier envelope 30 by means of a slot or similar bottom opening 36 positioned generally along the bottom edge 32 of side panels 31. Bottom opening 36 allows water which is poured through fill opening 8 to drain out of the barrier envelope 30 into the bottom portion 15 of inner bag 2 to become mixed with the chemical composition 3. In the preferred embodiment, bottom opening 36 is a narrow slot cut in the folded edge 32 where side panels 31 are joined together. The length of the slot is approximately 25–33% of the length of bottom edge 32. This amount of opening in the bottom of barrier envelope 30 in combination with the liquid fill opening 8 allows water which is added through liquid fill opening 8 to pass through the barrier envelope 30 to mix with chemical composition 3 contained in the bottom of inner bag 2.

Although water freely flows through these openings in barrier envelope 30, because of the size of bottom opening 36, and its location generally adjacent the fold line 29 along which the top portion 6 of inner bag 2 is folded, the granular chemical composition 3 is prevented from spilling out through opening 36 when the top portion 6 is folded over against bottom portion 15 of inner bag 2. To further prevent the spillage of the chemical composition 3 past the barrier envelope 30 and out of inner bag 2, a closure rivet 37 extends between front and back panels 9 and 10 of inner bag 2. In the preferred embodiment, closure rivet 37 is positioned generally adjacent bottom opening 36 at its midpoint. This further closes off bottom opening 36 to prevent the spillage of chemical composition 3 therethrough while still allowing water to freely flow through bottom opening 36. Barrier envelope 30 is fabricated from a flexible non-porous material which forms a moisture impervious trough in inner bag 2. In the preferred embodiment, a vinyl plastic material is utilized for this purpose.

When the top portion 6 of inner bag 2 is folded over, barrier envelope 30 tends to seal off any opening which may exist due to wrinkles or folds between the bottom portion 15 and the top portion 6 of inner bag 2. This allows the inner bag to be agitated or shaken to properly mix the water with the chemical composition 3 without spilling the mixture out of the inner bag 2. The stitching 13 which secures the side edges 34 of barrier envelope 30 between front and back panels 9 and 10 provides a sufficient seal around the edges of barrier envelope 30 such that water which is poured in through fill opening 8 will generally drain through bottom opening 36 rather than escape out of the barrier envelope 30. In this manner, barrier envelope 30 acts as a simple funnel apparatus for distributing the water from fill opening 8 into the inner bag bottom portion 15. In the manufacturing process, the chemical mix 3 can be added through bottom opening 36.

Figure 5:
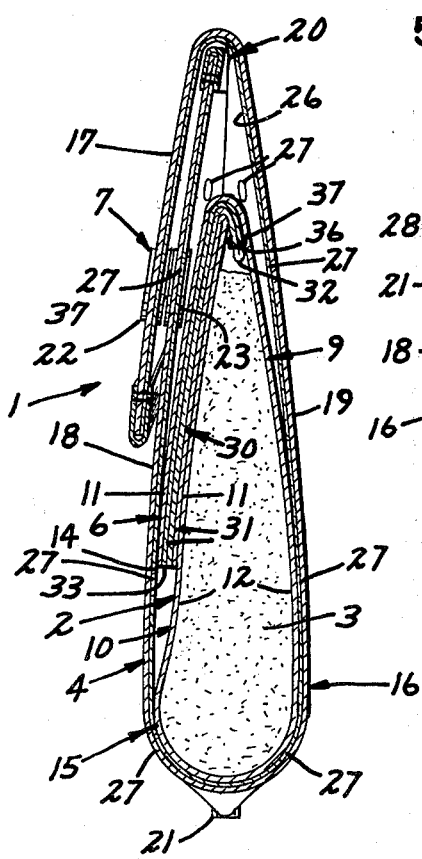
FIG. 5 is an enlarged sectional view as seen from line 5—5 of FIG. 4, showing the heating pack inner bag contained within the outer bag.
Figure 4:
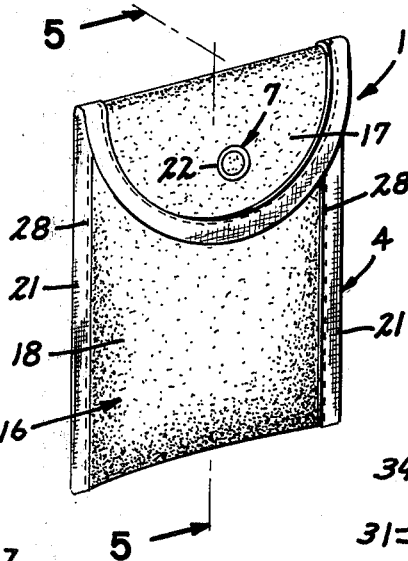
FIG. 4 is a side elevational view showing the heating pack inner bag contained within the outer bag.
Figure 6:
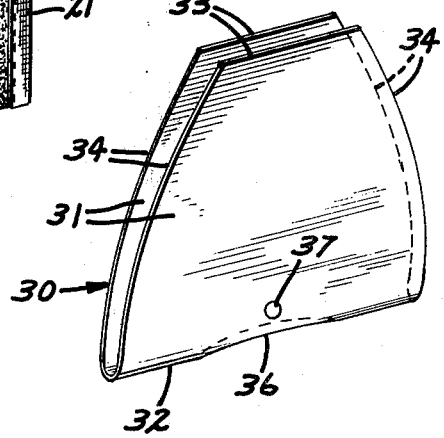
FIG. 6 is a perspective view of the barrier envelope.

Because it is necessary that water be added to the chemical composition 3 contained in the inner bag 2, there is a tendency for the inner bag 2 to become damp as the exothermic reaction continues. To prevent this dampness from being transmitted to the area which is being heated by the heating pack 1, e.g. the user's hands, the present invention provides an outer bag 4 into which inner bag 2 is inserted after top portion 6 of inner bag 2 has been folded over bottom portion 15. As is shown in FIGS. 1 and 4-5, outer bag 4 consists of a pocket portion 16 which is formed by joining opposed front and back panels, 18 and 19 respectively, together along their edges by means of a binding strip 21 and binding stitching 28. The top edge of the pocket portion 16 of outer bag 4 is left unstitched to provide an opening 20 for insertion of the inner bag 2. An outer closure flap 17 is attached to pocket portion 16 generally adjacent the top opening 20 and is foldable against the pocket portion 16 to partially cover over the pocket opening 12. A snap fastener 7 consisting of a top snap element 22 and a bottom snap element 23 is provided for fastening the outer closure flap 17 against the pocket portion 16. The top snap element 22 is fixed to the outer closure flap 17 and contains a snap detent 24 which engages a snap interlock 25 formed in the bottom snap element 23. The snap fastener 7 can be engaged and disengaged by pressing the top snap element 22 into snap element 23 as is well known in the art. Other suitable means for securing closure flap 17 in a closed position may also be utilized.

In the preferred embodiment shown in FIGS. 1-6, outer bag 4 is fabricated from a velour-like cotton fabric which is effective as a heat distributor that evenly distributes the heat across the surface of the outer bag 4. Other materials may also be utilized in practicing the present invention where they evenly conduct and distribute the heat through the outer bag 4.

To prevent moisture which is generated by the chemical reaction of chemical composition 3 from being absorbed into he soft fabric of outer bag 4, a vinyl lining 26 has been provided in the interior of outer bag 4. In the preferred embodiment shown in the figures, the vinyl lining 26 has the same contour as the outer bag panels 18 and 19 and is sewn or otherwise attached to the panels. Since it is desirable for a sufficient amount of air to penetrate both the outer and inner bags so as to reach the chemical composition 3, a plurality of holes 27 are contained in vinyl lining 26 to provide means for air to flow through the generally non-porous vinyl lining. By utilizing a plurality of relatively small openings 27, any moisture which is present on the surface of inner bag 2 is generally not absorbed directly by outer bag 4. However, some evaporation of water through openings 27 will allow the chemical composition 3 to eventually dry out which stops the chemical reaction.

The Heat-Producing Chemical Mixture

As is known in the art, ferrous materials (e.g. iron, steel, and combinations of iron or steel with iron oxides) can be oxidized in the presence of water (e.g. liquid water) to produce heat. This principle has been used in so-called chemically-fueled or "flameless" heating packs, and in other practical applications of heat-producing chemical compositions. It is also well-known that an oxidizing agent should be included in the chemical composition for efficient use of the ferrous material. Furthermore, dry iron particles (e.g. minus 100 U.S. mesh or smaller) can be blended or mixed in the dry state with dry particles of the oxidizing component, thereby providing a composition which is essentially inactive at room temperature in absence absense of moisture. Adding water to the composition activates the oxidation-reduction reactions and produces a significant evolution of heat. When heat is no longer desired, the reactants are allowed to return to the inactive, dry state through evaporation of moisture. The typical prior art oxidizing component contains material such as potassium chlorate, soluble or insoluble copper salts, halide salts, acidic materials, elemental carbon, ferrous or ferric salts (chlorides, sulfates, etc.), copper oxide, manganese salts or hydroxides, hygroscopic materials, dessicants, or varous combinations of these. Ammonium chloride is a particularly preferred halide, probably because of its acidity in aqueous media. Another acidic material preferred in the prior art is oxalic acid.

Literally decades of experience are associated with the task of formulating these water-activatable oxidation-reduction systems. Despite the depth of experience, however, formulation of a suitable oxidation-reduction system is not straightforward, since a number of desirable goals and necessary evils must be balanced against one another. For example, if the composition is formulated for fast heating (e.g. good heat production within 1 or 2 minutes), the life or number of wet/dry cycles obtainable from the composition may have to be reduced somewhat. Similarly, the desirability of a light weight composition must ordinarily be balanced against the number of wet/dry cycles which will be obtainable. Certain components preferred in the prior art can lead to specific problems, e.g. the production of undesirable odors from hydrolysis of ammonium chloride, problems of toxicity and/or contact dermititis with materials such as oxalic acid and other toxic inorganic or organic chemicals, etc.

It can be particularly difficult to achieve long life (e.g. 70 to 80 hours) along with both weight reduction and fast heating When the oxidizable component is iron or steel (both of which are relatively heavy materials), this component should be reduced in weight to obtain an overall weight reduction. (If light metals such as aluminum are used in place of iron, the composition can have the undesirable aspect of hydrogen evolution.) Loss of elemental iron will theoretically reduce the life of the composition also. This means that the oxidizing component must be carefully formulated to make efficient use of the iron that is available: that is, it is important that the exothermic oxidation-reduction reaction be stretched to its theoretical thermodynamic limits of heat evolution, both on a per-cycle basis and on an overall life-of-the-composition basis.

In studies done in connection with this invention, it has been found that:

a. it is desirable to use the combination of cupric carbonate and an alkali metal chlorate (e.g. potassium chlorate) as the oxidizing agent system. As is known in the art, the chlorate salt can oxidize elemental iron to iron oxides. According to the prior art, the cupric carbonate can be solubilized (e.g. by water in combination with an acid and preferably also a halide salt) to create conditions favorable for the Cu/Fe oxidation-reduction system in which iron "displaces" the copper from solution. Both of these reactions have been used in the prior art, individually, in combination with each other, and in combination with other oxidations-reduction sytems. In this invention, the combined oxidation system has been selected for maximum effectiveness, and cupric carbonate has been selected as the preferred copper salt.

b. the acidic constituent of the oxidizing component should be citric acid, rather than ammonium chloride, oxalic acid, or the like. Citric acid is non-toxic and non-odor producing. Furthermore, this particular solid organic acid appears to assist in some manner in providing the best overall oxidation-reduction system. The reason for this is not presently known. It is known that citric acid has a very unique chemical structure. All three of its carboxyl radicals have a $pK_a$ below 6.0, the first $pK_a$ being just slightly above 3.0. Furthermore, the acid contains one hydroxyl group and has chelating properties.

c. The amount of alkali metal chlorate is selected so as to provide maximum oxidizing efficiency with minimum loss of water from the system due to vaporization. With potassium chlorate, it is particularly important that the amount of solid chlorate in the oxidizing component be less than 12% by weight, so that vaporization loss is minimized. On the other hand, amounts of $KClO_3$ less than 6% by weight have been found to be relatively inefficient.

By following the teachings of this invention, it has been found that a variety of desirable objectives can be reached with 5 – 10 parts by weight of oxidizing components per 100 parts by weight of ferrous component, i.e. 5–10phr of oxidizable component based on ferrous material. The preferred ferrous material is cast iron filings, which can be minus 100 mesh or smaller, e.g. minus 200 U.S. mesh. The preferred amount of oxidizing mixture is 6–8 phr, based on iron. When the oxidizing component and the iron are blended, there is typically from 4.5–9% (e.g. 5–8%) oxidizing component, by weight, the balance being iron. If desired, the oxidizing component can contain an anti-caking amount of an anti-caking agent such as tricalcium phosphate or sodium silicoaluminate.

A typical heat-producing chemical composition of this invention is ordinarily provided by dry mixing the ingredients of the oxidizing component and then dry mixing the resulting component with the particulate iron. A typical iron/oxidizing component mixture obtained thereby is as follows:

Iron filings: 150–210 (e.g. 170–200) parts by weight.
Oxidizing component: 8–20 parts by weight.
For a chemically fueled hand warmer, the aforementioned amounts can be in grams.

The preferred formula for the oxidizing component is as follows:

| Ingredient | Broad-range, weight % | Preferred range, weight % | Optimum range, weight % |
| --- | --- | --- | --- |
| $CuCO_3$ | 20–50 | 25–35 | 29–31 |
| NaCl | 20–60 | 30–40 | 36–38 |
| Citric Acid | 15–40 | 20–30 | 24–26 |
| $KClO_3$ | 6–12 | 7–10 | 8–9.5 |

Use Of The Invention

The use and operation of heating pack 1 can be summarized as follows. An inner bag 2 is fabricated from a porous material, e.g. a cotton canvas fabric, to form a bag having a rectangular bottom portion 15 and a tapered top portion 6. A liquid fill opening 8 is provided in the tapered top portion for adding water to the interior of the bag 2. A non-porous barrier envelope 30 is sewn between the panels of top portion 6 to serve as a barrier to the granular chemical composition 3 which is contained in bottom portion 15 of the inner bag 2. A bottom opening 36 along the bottom edge of barrier envelope 30 provides a passageway between the liquid fill opening 8 and the bottom portion 15 of the inner bag. In use, water is added through the liquid fill opening 8 and flows down the trough provided by barrier envelope 30 and enters bottom portion 15 of the inner bag. To properly blend the water with the chemical composition, the bottom portion of the inner bag is agitated by finger motion or shaking which promotes mixing of the water with the chemical composition.

Either before or after the mixing of the chemical composition 3 with the water, the tapered top portion 6 of the inner bag 2 is folded down over the bottom portion 15 to partially enclose the chemical composition within the inner bag bottom portion. The inner bag 2 is then placed within the outer bag 4 and the outer bag closure flap 17 is folded down over the outer bag pocket portion 16 and snapped into place. The heating pack 1 is then ready for use. Heat is generated by the chemical process within a few minutes after the water has been added to the chemical composition. The level of heat produces and its duration will vary depending on the amount of chemicals and water which are contained in the inner bag. Generally, after the water has evaporated from the chemical composition, the chemical reaction will stop. When it is desired to again use the heating pack 1, the inner bag is removed from the outer bag and water is again added to the chemical composition to start the chemical reaction. The heating pack can be recycled in this manner many times and will have a total useful life of 70–80 hours or more.

What is claimed is:

1. In a heating pack comprising an outer bag and a removable inner bag for containing a particulate ferrous metal for producing an exothermic oxidation reaction in the presence of water, the improvement which comprises 6–8 parts by weight of an oxidizing mixture for use in combination with 100 parts by weight of said ferrous metal, said oxidizing mixture consisting essentially of:
- 25–35% by weight of cupric carbonate;
- 30–40% by weight of sodium chloride;
- 20–30% by weight of citric acid; and
- 7–10% by weight of potassium chlorate.

2. A heating pack according to claim 1 wherein said ferrous metal is cast iron filings and said oxidizing mixture consists essentially of:
- 29–31% by weight of cupric carbonate;
- 26–38% by weight of sodium chloride;
- 24–26% by weight of citric acid; and
- 8–9.5% by weight of potassium chlorate.

3. An improved container for a finely divided heat-producing chemical mixture which is activated by the addition of a liquid, comprising:
   a. a flexible bag having a lower pocket portion containing the chemical mixture and an upper flap portion, said flap portion foldable along a fold line from an open position wherein it is generally coplanar with said bottom portion to a closed position wherein it is positioned generally adjacent said lower pocket portion, wherein said bag is constructed of a porous material which contains the chemical mixture and permits the passage of gas therethrough to allow the chemical mixture to dry;
   b. said flap portion containing a fill opening through which the liquid can be added to the chemical mixture contained in the pocket portion;
   c. a barrier member constructed of generally non-porous material, said barrier member positioned within said first bag and separating said flap portion from said pocket portion to retard the spillage of the chemical mixture out of said pocket portion; and
   d. said barrier member containing a bottom opening which communicates between said fill opening and said pocket portion to allow the liquid to be added therethrough from said fill opening to said pocket portion while retarding the spillage of the chemical mixture therethrough when said flap portion is in its closed position.

4. The improved container of claim 3 wherein said heat-producing chemical mixture comprises a dry particulate mixture comprising about 5 to about 10 parts by weight of oxidizing component per 100 parts by weight of particulate ferous metal, said oxidizing component comprising:
- 20 – 50% by weight of cupric carbonate;
- 20 – 60% by weight of water soluble metal halide salt;
- 15 – 40% by weight of citric acid; and
- 6 – 12% by weight of alkali metal chlorate.

* * * * *